(12) United States Patent
Kemmis et al.

(10) Patent No.: US 7,344,729 B2
(45) Date of Patent: Mar. 18, 2008

(54) COMBUSTIBLE PESTICIDAL PRODUCTS

(75) Inventors: Bruce Graham Kemmis, Thornleigh (AU); Rosita Junus, Putney (AU)

(73) Assignee: Reckitt Benckiser (Australia) Pty Limited, Hull (GB)

( * ) Notice: Subject to any disclaimer, the term of this patent is extended or adjusted under 35 U.S.C. 154(b) by 579 days.

(21) Appl. No.: 10/362,062

(22) PCT Filed: Aug. 21, 2001

(86) PCT No.: PCT/GB01/03774

§ 371 (c)(1), (2), (4) Date: Jul. 9, 2003

(87) PCT Pub. No.: WO02/15689

PCT Pub. Date: Feb. 28, 2002

(65) Prior Publication Data

US 2004/0037779 A1    Feb. 26, 2004

(30) Foreign Application Priority Data

Aug. 22, 2000 (GB) ................................ 0020622.7

(51) Int. Cl.
 *A01N 25/20* (2006.01)
 *A01N 53/02* (2006.01)
(52) U.S. Cl. ............... 424/411; 424/409; 424/DIG. 10; 514/531; 514/919
(58) Field of Classification Search ............ 424/40–42, 424/402–421, 600–724, DIG. 10; 514/531
See application file for complete search history.

(56) References Cited

U.S. PATENT DOCUMENTS 3,257,267 A * 6/1966 Hay .............................. 162/159
5,096,539 A * 3/1992 Allan ............................. 162/9
5,447,713 A 9/1995 Elsner .......................... 424/40

FOREIGN PATENT DOCUMENTS

| FR | 2 705 530 | | 12/1994 |
|---|---|---|---|
| GB | 2 139 498 | * | 11/1984 |
| JP | 54076827 | * | 6/1979 |
| JP | 6055507 | * | 3/1994 |
| WO | 97 42814 | | 11/1997 |
| WO | 01 00105 A2 | | 1/2001 |
| WO | 01 00105 A3 | | 1/2001 |

OTHER PUBLICATIONS

PCT International Search Report, dated Oct. 18, 2001, for PCT/GB01/03774.
GB Search Report, dated Feb. 21, 2001, for GB 00220622.7.
WPI Abstract, Access No. 1995-016067 for FR 2705530.

* cited by examiner

*Primary Examiner*—Neil S. Levy
(74) *Attorney, Agent, or Firm*—Norris McLaughlin & Marcus, PA

(57) ABSTRACT

A combustible pesticidal product is disclosed which comprises a structural element formed from a cardboard having a thickness of at least 0.75 mm, a density of 450-850 $kgm^3$ and consisting of 1 or more plies, the cardboard including: an alkali or alkaline earth metal nitrate or nitrite in an amount of from 0 to 1.83% w/w, or an alkali or alkaline earth carbonate or bicarbonate in an amount of from 0.02 to 7.0% w/w; one or more mineral silicates in an amount of from 0.01 to 8.0% w/w; a phosphate in an amount of from 0.01 to 0.40% w/w and selected from the group consisting of diammonium phosphate, monoammonium phosphate, triammonium phosphate and mixtures thereof; a boron compound in an amount of from 0.001 to 0.92% w/w (as boron) and selected from the group consisting of boric acid, sodium tetraborate hydrous, sodium borate, potassium borate, calcium borate, zinc perborate, boronatrocalcite and mixtures thereof; one or more pesticides; and optionally a perfume and/or a dye, which product on combustion emanates the pesticide into the atmosphere. Typically the combustible product will be a mosquito coil which has been impregnated with one or more insecticides effective against mosquitoes. On combustion of the coil, insecticide is emanated into the atmosphere for a period of at least 4 hours. However, the coils of the invention may be active against mosquitoes for 8 hours or more.

43 Claims, No Drawings

COMBUSTIBLE PESTICIDAL PRODUCTS

This is an application filed under 35 USC 371 based on PCT/GB01/03774.

This invention relates to combustible products that emanate a pesticide into the atmosphere on combustion and more particularly to such products that undergo combustion for a prolonged period thereby providing an extended time period of pesticidal activity.

BACKGROUND ART

The kind of products to which this invention relates are commonly referred to as "mosquito coils". Such coils are characterised by being formed from a combustible material which is shaped into a circular helix. Included in the combustible material are one or more pesticides, which in the case of products active against mosquitoes will be insecticides. As the product burns, the insecticides are emanated into the atmosphere by virtue of their volatility. Ideally, such coils will provide an effective level of insecticide in the atmosphere for an appropriate time period.

Typically, mosquito coils are used in environments where persons sleep and are therefore unable to destroy mosquitoes before being bitten. Another usage is environments where infants or others incapable or having a limited ability of destroying attacking mosquitoes are placed.

It will be readily appreciated that mosquitoes are vectors for a number of particularly persistent and often life-threatening or at least debilitating diseases. Most significant among these diseases is malaria. It is therefore highly desirable to prevent mosquito bites as a means of preventing the contracting of such diseases.

Mosquitoes are particularly prevalent in tropical and sub-tropical regions. Many of these regions include countries with relatively low per capita incomes. It is therefore desirable to be able to provide pesticidal products that are highly cost effective. In general terms, traditional mosquito coils fulfil this role. They are relatively easy to form and include low cost ingredients. As emanation of the insecticide is only dependant on combustion of the coil, the only source of energy required is sufficient heat to initially ignite a coil to cause it to combust. However, one feature that is lacking in such coils is the ability to reliably provide a period of sufficient insecticidal activity while a person sleeps overnight. Typically coils should provide up to about 8 hours of insecticidal coverage. However, due to breakage, it is not uncommon for a coil to burn for a significantly shorter period of time. This requires that a person sleeping awake and recognise that the coil is not burning, then carefully relight the unbroken portion whilst ensuring that it is intact and correctly mounted. Such a requirement is not conducive to maintaining an effective overnight coverage against mosquito bites.

At this point it is worth noting that traditional mosquito coils are formed as planar circular helices in a moulding or other shaping process. At the terminal end of the coil, approximately in the centre, is a small aperture which is used to locate the mosquito coil on an upstanding pin. The upstanding pin usually projects out of a dish or tray which is used to collect the ashes of the combusted coil. Locating of the coil on the pin results in the coil separating out so as to form a continuous spiral with the beginning of the coil, which is where combustion commences, at a point lower than the terminal end which sits on the locating pin. In this way the continuous spiral forms a track which combusts from the outer beginning end to the mounted terminal end.

It should be appreciated that mosquito coils may also be formed as double circular helices. In these structures, the helices are formed co-terminously. However, prior to use, each helix must be separated out. One important reason for producing coils in this way is that of economical use of available material as well as ease of formation in manufacture.

As mentioned above, typically mosquito coils are subject to breakage. This arises out of the fact that they are quite brittle and during manufacture, rather than being produced in a planar form, coils may warp to assume a wavy or convex conformation. In some cases, a free end or tip of the coil may curl upwardly. It is therefore well recognised that breakage may occur during manufacture, packaging, transport and in use by a consumer. In this latter case, it is important that a consumer exercise considerable care in both opening and mounting a coil. More especially in the case of double helical coils, care must be taken in separating out each coil so as to avoid breakage. Again it must be emphasised that any breakage of a coil effectively results in a coil being shortened both in length and most significantly, burn time.

Whilst recognising the short comings of traditional mosquito coils, the present inventors have sought to provide an improved coil which is capable of providing a prolonged effective period of insecticidal coverage and is produced in a manner resulting in a cost effective product relative to the traditional coil.

This has been achieved by recognising that rather than using traditional fuel materials such as sawdust in the formulation of a mosquito coil, cardboard provides an effective fuel source and a prolonged burn time.

DISCLOSURE OF INVENTION

Accordingly, this invention consists in a first aspect in a combustible pesticidal product comprising a structural element formed from a cardboard having a thickness of at least 0.75 mm, a density of 450-850 kgm$^{-3}$ and consisting of 1 or more plies, the cardboard including:

an alkali or alkaline earth metal nitrate or nitrite in an amount of from 0 to 1.83% w/w, or an alkali or alkaline earth carbonate or bicarbonate in an amount of from 0.02 to 7.0% w/w;

one or more mineral silicates in an amount of from 0.01 to 8.0% w/w;

a phosphate in an amount of from 0.01 to 0.40% w/w and selected from the group consisting of diammonium phosphate, monoammonium phosphate and triammonium phosphate;

a boron compound in an amount of from 0.001 to 0.92% w/w (as boron) and selected from the group consisting of boric acid, sodium tetraborate hydrous, sodium borate, potassium borate, calcium borate, zinc perborate and boronatrocalcite;

one or more pesticides; and optionally a perfume and/or a dye, which product on combustion emanates the pesticide into the atmosphere.

In a second aspect, this invention further consists in the use of an alkali or alkaline earth metal nitrate or nitrite in an amount of from 0 to 1.83% w/w, or an alkali or alkaline earth carbonate or bicarbonate in an amount of from 0.02 to 7.0% w/w;

one or more mineral silicates in an amount of from 0.01 to 8.0% w/w;

a phosphate in an amount of from 0.01 to 0.40% w/w and selected from the group consisting of diammonium phosphate, monoammonium phosphate and triammonium phosphate;

a boron compound in an amount of from 0.001 to 0.92% w/w (as boron) and selected from the group consisting of boric acid, sodium tetraborate hydrous, sodium borate, potassium borate, calcium borate, zinc perborate and boronatrocalcite;

one or more pesticides; and optionally a perfume and/or a dye, in the manufacture of a cardboard-based combustible pesticidal product which on combustion emanates the pesticide into the atmosphere.

In a third aspect, the present invention still further consists in a method of forming a combustible pesticidal product comprising either incorporating into a cardboard during its preparation and/or applying to a cardboard as a coating thereof:

an alkali or alkaline earth metal nitrate or nitrite in an amount of from 0 to 1.83% w/w, or an alkali earth carbonate or bicarbonate in an amount of from 0.02 to 7.0% w/w;

one or more mineral silicates in an amount of from 0.01 to 8.0% w/w;

a phosphate in an amount of from 0.01 to 0.40% w/w and selected from the group consisting of diammonium phosphate, monoammonium phosphate and triammonium phosphate;

a boron compound in an amount of from 0.001 to 0.92% w/w (as boron) and selected from the group consisting of boric acid, sodium tetraborate hydrous, sodium borate, potassium borate, calcium borate, zinc perborate and boronatrocalcite;

one or more pesticides; and optionally a perfume and/or a dye.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Whilst this invention is applicable to a variety of pesticidal substances, the preferred form relates to the use of insecticides, particularly insecticides that are effective against mosquitoes. In this form, the invention comprises a mosquito coil. In such a preferred embodiment, the product is formed from a planar sheet of cardboard which is cut into the appropriate shape. Typically the shape will be helical although not necessarily circular. It should be noted that it is within the scope of this invention to utilise multi-sided structures as described in our co-pending British patent application no. 0018998.5 "Insecticidal Coil Structure".

For the purposes of describing this invention, reference will be made to mosquito coils, although it must be appreciated that this invention is not so-limited.

It is preferred that the one or more insecticides comprise substances which are toxic to mosquitoes. Without limitation, these include esbiothrin, d-allethrin, prallethrin, transfluthrin, bioallethrin, esbioallethrin, pyrethrins, citronella, pyrethroids, neem oil and mixtures thereof. When esbiothrin, d-allethrin, prallethrin, transfluthrin, bioallethrin, esbioallethrin, pyrethrins, and mixtures thereof are used, typically they will be in an amount of from 0.01 to 0.6% w/w, preferably to 0.02 to 0.3% w/w, most preferably 0.04 to 0.1% w/w. When pyrethroids, neem oil, citronella and mixtures thereof are used, typically they will be in an amount of from 0.01 to 10% w/w, preferably to 0.01 to 6% W/w, most preferably 0.04 to 6% w/w.

Emanation of the pesticide into the atmosphere occurs as a result of the pesticide being volatilised as the coil burns. At the front or tip of combustion of a coil, the temperature may be 200-500° C. However, behind the tip, the temperature will be somewhat lower owing to the insulation properties of the cardboard. This means that compounds such as esbiothrin which boil at 160-170° C. will be volatised and released into the atmosphere behind the burning tip. Without being bound by theory, the present inventors believe that the efficacy of this invention may be due to less of a temperature gradient between the burning tip and the remainder of the coil. This results in a more effective temperature distribution across the coil thus allowing for the use of lower levels of pesticide than would usually be used.

The cardboard includes an alkali or alkaline earth metal nitrate or nitrite in an amount of from 0 to 1.83% w/w. Preferably, the alkali or alkaline earth metal nitrate or nitrite will be included in an amount of from 0.04 to 1.83% w/w, most preferably about 0.04 to 0.15% w/w. The nitrates or nitrites that may be used include sodium, potassium, calcium, magnesium and mixtures thereof. It is preferred to utilise potassium as the nitrate or the nitrite, preferably as the nitrate.

As an alternative to the alkali earth metal nitrate or nitrite, the cardboard may include an alkali earth carbonate or bicarbonate in an amount of from 0.02 to 7.0% w/w. Preferably the alkali earth metal carbonate or bicarbonate will be included in an amount of from 0.02 to 3.5% w/w, most preferably 0.82 to 1.83% w/w. The carbonates or bicarbonates that may be used include sodium, potassium, calcium, magnesium and mixtures thereof. It is preferred to use potassium carbonate.

One or more mineral silicates are included in the cardboard in an amount of from 0.01 to 8.0% w/w. Preferably, the mineral silicates are included in an amount of from 0.01 to 4.0% w/w, most preferably 1.5 to 3.5% w/w. As used in this specification, mineral silicates refers to silicate compounds which may include cations such as sodium, potassium, calcium magnesium and aluminium. A preferred mineral silicate is sodium silicate. Likewise, the concentration of silicates referred to herein is determined using the ASTM Designation D3683-94 "Standard Test Method for Trace Elements in Coal and Coke Ash by Atomic Absorption, section 9.2".

A phosphate in an amount of from 0.01 to 0.40% w/w and selected from the group consisting of diammonium phosphate, monoammonium phosphate, triammonium phosphate and mixtures thereof is included in the cardboard. Preferably the phosphate is included in an amount of from 0.02 to 0.40% w/w, most preferably about 0.14% w/w. Furthermore, of these phosphates, diammonium phosphate is preferred.

A boron compound in an amount of from 0.001 to 0.92% w/w (as boron) and selected from the group consisting of boric acid, sodium tetraborate hydrous, sodium borate, potassium borate, calcium borate, zinc perborate, boronatrocalcite and mixtures thereof is included in the cardboard. Preferably the boron compound is included in an amount of from 0.005 to 0.92% w/w, most preferably 0.01 to 0.92% w/w (as boron). Furthermore, of these boron compounds, sodium borate is preferred.

It is within the scope of this invention to include a perfume and/or a dye. Both the perfume and the dye, if included, will be selected on the basis of satisfying specific organoleptic requirements. It will of course be appreciated that the perfume must be suitably stable under the conditions of combustion of the coil.

In a preferred embodiment, the structural element is made from cardboard comprising 1 to 12 plies, preferably 2 or more plies, most preferably 3 plies, especially 4 plies. Whilst the thickness of the cardboard will be from 0.75 to 3.8 mm, preferably it will be at least 2 mm, most preferably at least 2.6 mm, especially 3.0 to 3.5 mm.

It has been found that the density of the cardboard is of importance. To achieve appropriate burn times, the cardboard has a density of 450-850 $kgm^{-3}$, preferably 600-700 $kgm^{-3}$, most preferably 650-690 $kgm^{-3}$.

The cardboard may be manufactured from a variety of pulp types including recycled pulp, Kraft pulp and thermomechanical pulp. Of these, recycled pulp is preferred as it assists in maximising combustion time of the pesticidal product.

Within the pulp and indeed as an adherent for the plies of cardboard, starch may be used. A typical pulp may include 5 to 8% w/w of starch. For the purposes of the present invention, an overall additional amount of about 2 to 5% w/w may be included in the cardboard of the invention.

It will of course be appreciated that "paper" falls within the definition of "cardboard" as used in this specification.

Broadly speaking, the various materials to be included in the cardboard may be either incorporated during the preparation of the cardboard, applied as a coating after the cardboard has been formed or both incorporated and applied as a coating.

When a coating is applied, it is important to note that certain of the materials cannot be dissolved in the same solution for coating purposes. For example, the alkali earth metal nitrate or nitrite and the mineral silicates may be dissolved in the same aqueous solution. Likewise, the alkali metal carbonate or bicarbonate and the mineral silicates; the alkali metal nitrate or nitrite and the phosphate and the alkali metal nitrate or nitrite may each be dissolved in the same aqueous solution.

Whilst the aforementioned materials may be applied as aqueous solutions, the one or more pesticides and the perfume are not generally water soluble. Accordingly, either or both of these materials may be added to the aqueous solution of the other materials along with an emulsifier to ensure that they are uniformly dispersed. Alternatively, they may be dissolved in a solvent and separately applied either before or after the aqueous coating(s).

The inclusion of a dye is optional and depending on the selected dyes solubility may be incorporated in an aqueous solution or in a suitable solvent for separate addition as a coating. If it is incorporated in a non-aqueous solvent, then preferably the solvent will be chosen to dissolve the perfume and the one or more pesticides.

If the dye is incorporated as an aqueous solution, it may be thickened with a suitable thickening agent such as guar gum to form a paste so as to allow application by painting or rolling.

It therefore follows that to apply all of the materials as a coating, a plurality of coatings are required. In such circumstances, drying may be carried out to remove excess water between each coating.

Alternatively, all coatings may be sequentially applied and the resultant coated cardboard dried.

Typically the coat weight before drying will be in the range of from 5 to 240 $gm^{-2}$, preferably 5-50 $gm^{-2}$. In those instances where all of the materials are applied as a coating, the coat weight is most preferably 30-50 $gm^{-2}$.

Application of the coatings may occur using techniques such as rolling, painting, printing or spraying. Naturally, the materials must be dissolved or dispersed in a liquid that is capable of application, desirably to obtain a uniform coating. If printing is used, well known techniques such as offset printing, gravure printing and lithographic printing may be used.

Conveniently, application would usually be made to one of the planar surfaces of the cardboard although both opposing outer surfaces could be coated if required.

In order to produce the requisite structural element, an appropriately dimensioned knife is used to cut out the structure from a sheet of cardboard. The resultant structural element may be in the form of a single helix or a double helix. A double helix structure is preferred as such a structure has the benefit of providing two, separable combustible pesticidal products. In this embodiment, the helices will interlock over their full length.

The cardboard may be cut in a manner so as to create a product in which each of the helices remain connected by virtue of the cutting incompletely severing the cardboard. An embodiment of this type may be prepared in which a bridge, being a thin section of cardboard, is formed between adjacent portions of a helix. Such embodiments are advantageous as they provide structural support for the product. This allows for the ready packaging and shipment of the product whilst permitting a consumer to easily separate each helix from the other prior to use. In addition, it will be appreciated that a cutting knife to form such embodiments will consist of a number of separate knife segments. Thus if any knife segment is damaged, the damaged segment may be readily replaced. By contrast, when a single cuffing knife is used, any damage to the knife requires complete replacement and hence greater cost.

Alternatively, cutting of the cardboard may be done in a manner such that the cardboard is completely severed. In this case, a single knife is used rather than segmented knives as described above. Whilst this has the disadvantage relative to the use of segmented knives in relation to knife damage, nevertheless it is a viable and practical option for the preparation of cardboard coils.

When produced as mosquito coils, the products of the invention may burn typically for up to 24 hours. By adjusting parameters such as the density, thickness, number of plies and mass of coil, various burn times may be obtained. For example, burn times of at least 4 hours, preferably at least 8 hours, most preferably at least 12 hours may be obtained. It will also be appreciated that the amount of the various additives such as the alkali earth metal nitrate or nitrite, the mineral silicates, the phosphate and the boron compound will affect burn time.

In order to better understand the nature of the invention, a number of examples will now be described.

MODES FOR CARRYING OUT THE INVENTION

A number of examples were prepared without the inclusion of a pesticide and their burn times were evaluated as follows. It should be noted the concentrations of ingredients in the examples refer to the concentrations of materials added to the pulp or cardboard as may be the case. These concentrations do not take into account any ingredients that may have been present in the pulp or cardboard before addition of the ingredients required by the invention.

EXAMPLE 1

Board: recycled, single ply, contains 10% starch, density 690 $kgm^{-3}$, thickness 3.6 mm, weight of single coil ~15 g.
Additives: added to the pulp, final concentrations in the dry board are 1.108% w/w Potassium Nitrate and 0.554% w/w Sodium Silicate.
Burn time (72 cm length coil): 7 hrs 50 mins-8 hrs 3 mins (average 7 hrs 58 mins)

EXAMPLE 2

Board: recycled, single ply, contains 10% starch, density 685 $kgm^{-3}$, thickness 3.6 mm, weight of single coil 15 g.
Additives: Sprayed onto the coils on both sides. Additive solution contains: 7.5% w/w Potassium Carbonate and 5% w/w Sodium Silicate (balance: water).
Coat weight: 38 $gm^{-2}$. Final concentrations in the coil after drying: 0.12% w/w Potassium Carbonate and 0.08% w/w Sodium Silicate.
Burn time (72 cm length coil): 6 hrs 3 mins-6 hrs 19 mins (average 6 hrs 11 mins).

EXAMPLE 3

Board: recycled, 4 ply PVA laminated, density 587 $kgm^{-3}$, thickness 3.0 mm, weight of single coil ~11 g
Additives: Sprayed on both sides. First coating: 6% w/w Sodium Borate in water at 104 $gm^{-2}$ coat weight (giving 0.35% w/w in the coil after drying).
Second coating: 7.5% w/w Potassium Carbonate and 5% w/w Sodium Silicate in water at 65 $gm^{-2}$ coat weight (giving 0.28% w/w Potassium Carbonate and 0.18% w/w Sodium Silicate in the coil after drying).
Note: The coil was not dried between the first and second coatings.
Burn time (72 length cm coil): 4 hrs 28 mins A number of examples of mosquito coils were prepared incorporating active insecticides as follows:

EXAMPLE 4

Board: recycled, 4 ply PVA laminated, density 587 $kgm^{-3}$, thickness 3.0 mm, weight of single coil ~11 g
Additives: Sprayed onto the coils on both sides. Additive solution contains: 10% w/w Potassium Nitrate and 5% w/w Sodium Silicate (balance: water). Coat weight: 50 gm-2. Final concentrations in the coil after drying: 0.28% w/w Potassium Nitrate and 0.14% w/w Sodium Silicate. After drying, the coils were sprayed with insecticide active in solvent. The solvent used was Norpar 12 (RTM available from Exxon) but other hydrocarbon solvents such as Norpar 13 or Exxsol D80 (RTM available from Exxon) may also be used. Concentration of the active was adjusted to obtain the desired level of active in the coil. After spraying the coils were air dried at room temperature until the solvent evaporated.

The efficacy test results are as follows (small chamber test on *Aedes aegypti* mosquitoes):
Lot 1 (the Cardboard Coils were Sprayed with the Active on Both Sides)

| Coil: | KD50 (+/- 95% confidence intervals) |
|---|---|
| Example 5 | |
| Cardboard, Esbiothrin 0.07% w/w | 81.5 (75.6-87.2) |
| Example 6 | |
| Cardboard, Prallethrin 0.02% w/w | 88.2 (77.2-98.8) |
| Comparative coil, Esbiothrin 0.1% w/w | 81.5 (74.9-87.6) |

Notes:
KD50 is the time (in seconds) to reach knockdown of 50% of the mosquito population.

Statistical analysis indicates that the efficacies of the three coils above are not significantly different at the 5% level.

Lot 2 (the Cardboard Coils were Sprayed with the Active on One Side)

| Coil: | KD50 (+/-95% confidence intervals) |
|---|---|
| Example 7 | |
| Cardboard, Esbiotbrin 0.07% w/w | 79.0 (72.3-85.2) |
| Example 8 | |
| Cardboard, Esbiothrin 0.04% w/w | 82.6 (73.9-90.5) |
| Comparative coil, Esbiothrin 0.1% w/w | 74.1 (67.0-80.6) |

Statistical analysis indicates that the efficacies of the three coils above are not significantly different at the 5% level.

It is important to note that in each of the examples 5-8, the level of active used was substantially less than that used in the comparative examples and yet comparable efficacy was achieved. This indicates that a substantial advantage of the coils of the invention is that a reduced level of active insecticide may be used to achieve a suitable level of efficacy.

Two further examples were prepared and tested as follows:

EXAMPLE 9

Cardboard: recycled, grey board, 4 ply laminated with hydrolysed starch, density 630 $kgm^{-3}$, thickness 3.8 mm, weight of single coil 18 g. The cardboard contained 0.22% w/w of nitrate and 3.8% w/w of mineral silicates.

The burn time for a number of tests was found to range between 6 hrs 5 mins-7 hrs 25 mins (average 6 hrs 38 mins).

EXAMPLE 10

Cardboard: recycled, grey board, 3 ply PVA laminated, density 620 $kgm^{-3}$, thickness 3.0 mm, weight of single coil 14.5 g. The cardboard contained 4.4% w/w mineral silicates. The burn time for a number of tests was found to range between 6 hrs 55 mins-7 hrs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A combustible insecticidal product effective against flying insects comprising a structural element formed from a pulp based cardboard having a thickness of at least 0.75 mm, a density of 450-850 kgm$^{-3}$ and consisting of at least one ply, the cardboard comprising:
   an alkali or alkaline earth metal nitrate or nitrite in an amount of from 0.04 to 1.83% w/w, or an alkali or alkaline earth carbonate or bicarbonate in an amount of from 0.02 to 7.0% w/w;
   at least one mineral silicate in an amount of from 0.01 to 8.0% w/w;
   a phosphate in an amount of from 0.01 to 0.40% w/w and selected from the group consisting of diammonium phosphate, monoammonium phosphate and triammonium phosphate;
   a boron compound in an amount of from 0.001 to 0.92% w/w as boron and selected from the group consisting of boric acid, sodium tetraborate hydrous, sodium borate, potassium borate, calcium borate, zinc perborate and boronatrocalcite;
   at least one insecticide effective against flying insects and selected from the group consisting of esbiothrin, d-allethrin, pralletrhrin, transfluthrin, bioallethrin, esbioallethrin, pyrethrins, pyrethroids, citronella, neem oil and mixtures thereof; and optionally
   a perfume and/or a dye,
   wherein the product an combustion emanates the insecticide into the atmosphere.

2. A combustible insecticidal product as in claim 1 wherein the alkali or alkaline earth metal nitrate or nitrite is in an amount of from 0.04 to 1.83% w/w.

3. A combustible insecticidal product as in claim 2 wherein the alkali or alkaline earth metal nitrate or nitrite is in an amount of from 0.04 to 0.15% w/w.

4. A combustible insecticidal product as in claim 1 wherein the alkali or alkaline earth carbonate or bicarbonate is in an 35 amount of from 0.02 to 3.5% w/w.

5. A combustible insecticidal product as in claim 4 wherein the alkali or alkaline earth carbonate or bicarbonate is in an amount of from 0.02 to 1.83% w/w.

6. A combustible insecticidal product as in claim 1 wherein the at least one mineral silicate is in an amount of from 0.01 to 4.0% w/w.

7. A combustible insecticidal product as in claim 6 wherein the at least one silicate is in an amount of from 1.5 to 3.5% w/w.

8. A combustible insecticidal product according to claim 1, wherein the insecticide is esbiothrin.

9. A combustible insecticidal product according to claim 1 wherein the at least one insecticide is present in an amount of from 0.01 to 0.6% w/w.

10. A combustible insecticidal product as in claim 9, wherein the at least one insecticide is in an amount of from 0.02 to 0.3% w/w.

11. A combustible insecticidal product as in claim 10, wherein the at least one insecticide is in an amount of from 0.04 to 0.1% w/w.

12. A combustible insecticidal product as in claim 1 wherein the at least one insecticide is selected from the group consisting of pyrethroids, neem oil, citronella and mixtures thereof and is in an amount of from 0.01 to 10% w/w.

13. A combustible insecticidal product as in claim 12, wherein the at least one insecticide is in an amount of from 0.01 to 6% w/w.

14. A combustible insecticidal product as in claim 12, wherein the at least one insecticide is in an amount of from 0.04 to 6% w/w.

15. A combustible insecticidal product as in claim 1 wherein the nitrate or nitrite is selected from the group consisting of sodium nitrite, sodium nitrate, potassium nitrate, potassium nitrite, calcium nitrate, calcium nitrite, magnesium nitrate, magnesium nitrite and mixtures thereof.

16. A combustible insecticidal product as in claim 15 wherein the nitrate or nitrite is potassium nitrate or potassium nitrite.

17. A combustible insecticidal product as in claim 16, wherein the nitrate or nitrite is potassium nitrate.

18. A combustible insecticidal product as in claim 1 wherein the carbonate or bicarbonate is selected from the group consisting of sodium carbonate, sodium bicarbonate, potassium bicarbonate, potassium carbonate, calcium bicarbonate, calcium carbonate, magnesium bicarbonate, magnesium carbonate and mixtures thereof.

19. A combustible insecticidal product as in claim 18 wherein the carbonate or bicarbonate is potassium carbonate.

20. A combustible insecticidal product as in claim 1 wherein the phosphate is an amount of from 0.02 to 0.40% w/w.

21. A combustible insecticidal product as in claim 20, wherein the phosphate is an amount of about 0.14% w/w.

22. A combustible insecticidal product as in claim 20 wherein the phosphate is diammonium phosphate.

23. A combustible insecticidal product as in claim 1 wherein the boron compound is in an amount of from 0.005 to 0.92% w/w as boron.

24. A combustible insecticidal product as in claim 23, wherein the boron compound is in an amount of from 0.01 to 0.92% w/w as boron.

25. A combustible insecticidal product as in claim 1 wherein the boron compound is sodium borate.

26. A combustible insecticidal product as in claim 1 wherein the product is formed from cardboard comprising from 1 to 12 plies.

27. A combustible insecticidal product as in claim 26 wherein the cardboard is comprised of at least 2 plies.

28. A combustible insecticidal product as in claim 27, wherein the cardboard is comprised of 3 plies.

29. A combustible insecticidal product as in claim 27, wherein the cardboard is comprised of 4 plies.

30. A combustible insecticidal product as in claim 26 wherein the thickness of the cardboard is from 0.75 mm to 3.8 mm.

31. A combustible insecticidal product as in claim 30, wherein the thickness is at least 2 mm.

32. A combustible insecticidal product as in claim 30, wherein the thickness is at least 2.6 mm.

33. A combustible insecticidal product as in claim 27 wherein the thickness of the cardboard is from 0.75 mm to 3.8 mm.

34. A combustible insecticidal product as in claim 27, wherein the thickness is at least 2 mm.

35. A combustible insecticidal product as in claim 27, wherein the thickness is at least 2.6 mm.

36. A combustible insecticidal product as in claim 30 wherein the thickness of the cardboard is 3.0 mm to 3.5 mm.

37. A combustible insecticidal product as in claim 1 wherein the density of the cardboard is from 600-700 kgm$^{-3}$.

38. A combustible insecticidal product as in claim 37, wherein the density is 650-690 kgm$^{-3}$.

39. A combustible insecticidal product as in claim 1 wherein the product is a mosquito coil having a burn time of at least 4 hours.

40. A combustible insecticidal product as in claim 39 wherein the burn time is at least 8 hours.

41. A combustible insecticidal product as in claim 39 wherein the burn time is at least 12 hours.

42. A mosquito coil comprising a combustible insecticidal product as in claim 1.

43. A method of forming a combustible insecticidal product effective against flying insects comprising incorporating into a pulp based cardboard during its preparation and/or applying to a pulp based cardboard as a coating thereof:

an alkali or alkaline earth metal nitrate or nitrite in an amount of from 0.04 to 1.83% w/w, or an alkali or alkaline earth carbonate or bicarbonate in an amount of from 0.02 to 7.0% w/w;

at least one mineral silicate in an amount of from 0.01 to 8.0% w/w;

a phosphate in an amount of from 0.01 to 0.40% w/w and selected front the group consisting of diammonium phosphate, monoammonium phosphate and triammonium phosphate;

a boron compound in an amount of from 0.001 to 0.92% w/w as boron and selected from the group consisting of boric acid, sodium tetraborate to hydrous, sodium borate, potassium borate, calcium borate, zinc perborate and boronatrocalcite;

at least one insecticide effective against flying insects and selected from the group consisting of esbiothrin, d-allethrin, pralletrhrin, transfluthrin, bioallethrin, esbioallethrin, pyrethrins, pyrethroids, citronella, neem oil and mixtures thereof; and optionally a perfume and/or a dye wherein the combustible insecticidal product, in use, emanates the insecticide into the atmosphere.

* * * * *